(12) United States Patent
Barnes

(10) Patent No.: US 6,285,730 B1
(45) Date of Patent: Sep. 4, 2001

(54) DUST/PARTICLE MONITOR

(75) Inventor: Roger Neville Barnes, Billericay (GB)

(73) Assignee: CODEL International Ltd. (GB)

( * ) Notice: Subject to any disclaimer, the term of this patent is extended or adjusted under 35 U.S.C. 154(b) by 0 days.

(21) Appl. No.: 09/338,177

(22) Filed: Jun. 22, 1999

(30) Foreign Application Priority Data

Jun. 27, 1998 (GB) .................................................. 9813858

(51) Int. Cl.$^7$ .................................................. G06M 11/00
(52) U.S. Cl. .................................. 377/10; 377/11; 377/12; 377/19
(58) Field of Search .................................. 377/10, 11, 12, 377/19

(56) References Cited

U.S. PATENT DOCUMENTS

| | | | |
|---|---|---|---|
| 3,675,768 | * | 7/1972 | Legorreta-Sanchez .................. 209/4 |
| 6,032,804 | * | 3/2000 | Paulson ................................. 209/148 |

* cited by examiner

Primary Examiner—Margaret R. Wambach
(74) Attorney, Agent, or Firm—Trexler, Bushnell, Giangiorgi, Blackstone & Marr, Ltd.

(57) ABSTRACT

The invention relates to dust/particle monitors, and particularly but not necessarily exclusively to a method of monitoring fine particles harmful to humans in working environments. Equipment and methods of detection are known but which have several disadvantages such as no instantaneous warnings of excessive exposure, bulky sampling equipment, prone to errors due to poor handling of particles, and fluctuating flow rates of air borne particles. The object of the invention is to provide a method and equipment that avoids those disadvantages mentioned above, an objective met by a method of monitoring dust/particulate material concentrations in air, comprising drawing air through a monitor at a predetermined rate to enable particles to pass through a measurement section one at a time, whereby they may be individually detected and counted. An optical detection and counting system may be employed, but preferably an electrode is located in the measurement section on which an individual particle induces a pulse of charge, and there being a means of counting the number of pulses of charge induced on the electrode in unit time, from which the concentration of dust particles in the air in the vicinity of the monitor can readily be derived.

6 Claims, 6 Drawing Sheets

DUST/PARTICLE MONITOR

BACKGROUND

The invention relates to dust/particle monitors, and particularly but not necessarily exclusively to a method of monitoring fine particles harmful to humans in working environments.

As a result of industrial processing of materials, fine particulate is generated which may be harmful to a workforce. Particulate less than 7.5 μm in diameter attaches to the human pharynx, bronchi and alveoli, leading, after long term exposure, to several serious respiratory conditions. Government places strict Occupational Exposure Limits (based on a time weighted average) on employers to restrict the amount of airborne contamination a worker may inhale over a given time period.

The recognised technology used for measuring the concentration of fine particulate inhaled consists of a regulated vacuum pump (flow rate 2–4 liters per minute) worn on a harness connected by means of a tube to a sampling head placed within a persons breathing zone to sample the microenvironment to which the person is exposed.

The air is drawn into the sampling head and through a pre-weighed filter paper by the pump. As particulate is deposited on to the filter paper, the flow rate diminishes due to increasing back pressure and the speed of the pump is regulated to keep the flow rate constant. At the end of a period of time, the filter is removed, dried and re-weighed on a micro-balance. The weight of the filtered particulate is calculated and then using the following calculation, the time weighted average concentration is derived.

$$\text{Concentration in mg/m}^3 = \frac{W \times 1000}{F \times ST}$$

Where

W=weight of particulate

F=flow rate in 1/min

ST=sampling time

To limit the particulate size range into the sampling head to a desired range (normally Total Respirable Dust up to 7.5 μm) the air containing the dust is first passed through a cyclone separator so as to remove dust particles above 7.5 μm. The volumetric air flow rate through a cyclone separator must run at a specific volumetric flow rate in order to separate particles above a given size accurately.

The disadvantages of the present method are:

1. No instantaneous warning of excessive exposure either due to very high immediate levels or long term excessive exposure.
2. Bulky sampling equipment with associated high noise levels.
3. Errors introduced into results due to poor handling, drying and weighing of filter media.
4. Fluctuating flow rate due to use of diaphragm (reciprocating) vacuum pumps and inadequate pump speed controllers lead to inaccurate flow rate estimation and inefficient cyclone separation efficiency.

The mechanism of detecting air borne particulates, using charge induction techniques, involves causing the air or gas in which the particulates are suspended to pass through a duct or pipe in which there is an associated sensing electrode or electrodes. Provided there is some charge on a particle the movement of the particle pass the electrode causes a varying charge to be induced on the electrode which causes a varying current to flow in the electrode which may be detected using appropriate electronic signal processing.

The mechanisms whereby particles become electrically charged are many, and the magnitude of charge associated with a particle depends on many factors such as particle size, particle shape, particle material, the level of moisture, and particularly the charging history of the particle. In many industrial processes, where dusts are formed during the processing and/or movement of bulk solid materials, the magnitude of charges produced on the particles is of a sufficient level for detection.

On the other hand where dust has rested on a surface for some time the charge may be partially or completely lost due to conduction of the charge to ground. If the dust is then lifted into the air by air movement over the dust laden surface the magnitude of charge on the particles may be too small to measure.

Because of the variable nature of the magnitude of the charges resident on air borne particles, methods of estimating the quantity of dust based on overall charge values are subject to considerable and unknown errors. This problem is further aggravated in that the mechanism of sensing charge induced onto electrodes involves a process of differentiation (as described below) so that only a change in induced charge in the sensing electrode can be measured.

In the case where a cloud of particles is passing the electrode, the induced charge on the sensing electrode is the sum of all of the individual induced charges from each particle and the output voltage from the signal processing system will be proportional to the derivative of the summed charge signal.

The resulting output voltage will be a noise signal which can be processed on-line by deriving, for example, the rms value, or the absolute value of the signal. However, these parameters of the noise signal are only loosely related to the total charge on the dust cloud due to the inherent differentiation process relating the current flowing in the electrode to the induced charge.

Not-with-standing these inherent problems, in the past attempts have been made to measure dust concentrations using these techniques by calibrating instruments with known concentration levels of dust and particulates.

The difficulty with measurements based on this approach (apart from the differentiation problem mentioned above) is that the calibration is not stable because the factors which determine the magnitude of charge on the particles may vary with time.

An illustration of the method of detecting particles using electrostatic techniques is shown in FIG. 1 which is a schematic sectional elevation of the volume below a charge distribution curve. A single particle 1 at position A has an electric charge of +q coulombs on it, and it is at a distance of d from the duct wall 2 and a lateral distance of l from the position of the sensing electrode 3. The duct wall is an electrical conductor and is at earth potential. The sensing electrode is attached to the outside surface of an insulating section 4 of the duct wall and is connected to the inverting input of an operational amplifier 5 which will also be at earth potential as it is a virtual earth point. The electrode is shown as mounted on the outside surface of the insulating section so as to avoid the possibility of particles colliding with the electrode and causing charges to be placed directly on the electrode by the tribo-electric effect. Alternatively the electrode may be mounted on the inside surface but with a thin layer of insulation.

The charge of +q Coulombs on the particle will cause there to be a charge of opposite polarity induced on the earthed conducting surfaces of the duct wall and the sensing electrode (which is also at earth potential) as shown by the curve 6 of FIG. 1. The distribution of the charge on the duct wall 2 and electrode 3 is as shown by the curve 6 of FIG. 1, and the total charge induced on the duct wall and the sensing electrode is represented by the area under the curve 6 and will be −q Coulombs. The fraction of the charge that appears on the sensing electrode 3 will be equal to the ratio of the shaded volume of the charge distribution immediately above the electrode to the total volume under the charge distribution curve.

If we now consider the particle to be moving at constant velocity to the right and parallel to the plate, the fraction of the charge intercepted by the sensing electrode 3 will vary as a function of time as shown in the graph of FIG. 2(*a*).

As a result of the charge varying on the electrode with time and as is indicated in FIG. 1, a current $I_e$ will flow between the electrode and the virtual earth of the amplifier according to the equation:

$$I_e = dq/dt \qquad (1)$$

The current waveform is shown in FIG. 2(*b*) and will produce a voltage Vo at the output of the operation amplifier which is given by the relationship:

$$Vo = -R.I_e \qquad (2)$$

The voltage waveform Vo shown in FIG. 2(*c*) will be the same shape as the current waveform $I_e$ shown in FIG. 2(*b*), but it will be inverted due to the action of the operational amplifier.

In effect, the operational amplifier output voltage waveform Vo is equivalent to the time derivative of the charge waveform intercepted by the sensing electrode. The output voltage of the operational amplifier will have fallen to approximately a tenth of the maximum signal zero when the particle is at a position where the lateral displacement is three times the distance between the particle and the duct wall as discussed above.

The difficulty in this approach is that the calibration is not stable. The reasons for this are that the electric charge on each particle depends on several factors mentioned above that can not be controlled or independently measured.

SUMMARY

The object of the present invention is to provide for dust/particulate material monitoring to enable the immediate signalling of harmful levels of harmful dust and particles, with the avoidance of those disadvantages mentioned above.

According to the present invention, a method of monitoring dust/particulate material concentrations in air, comprises drawing air through a monitor at a predetermined rate to enable particles to pass through a measurement section one at a time, whereby they may be individually detected and counted. An optical detection and counting system may be employed, but preferably an electrode is located in the measurement section on which an individual particle induces a pulse of charge, and there being a means of counting the number of pulses of charge induced on the electrode in unit time, from which the concentration of dust particles in the air in the vicinity of the monitor can readily be derived.

To guard against dust particles having such a low charge as to be substantially undetectable, it is preferred that the dust monitor of the invention is provided with a means of inducing a charge on the dust particles as they pass through it. Thus, and for example, a rotating filter may be provided in the flow path from an inlet to the measurement section, whereby particles are first caught and then thrown from the filter, to induce a charge on an uncharged particle or increase the charge on a charged particle by the tribo-electric effect, the degree of induced charge being proportional to their surface area, whereby to enable a pulse of charge to be induced on the electrode.

The equipment to enable the above method to be operated can be simple and of light weight, and hence easily carried by an operative. A relatively small fan motor is required to draw required volumes of air through the monitor, easily driven by a relatively small battery.

A digital recording means for storing the shape and count of pulses for subsequent analysis can be provided, and the monitor can be provided with a relatively simple visual or audible signal means to warn an operative that a predetermined level of dust concentration in the air has been reached.

The invention therefore, not only allows a monitor to be carried with ease and provide an immediate warning signal, but also makes it possible that successive measurements of this type can be stored over an extended period of time, and the resulting data file can be used in a number of ways. Firstly the variation of the concentration as a function of time can be deduced and secondly the average number of particles over the extended period of time can be deduced.

Furthermore, if the type of dust passing through the instrument is known, in terms of it's particle size distribution as obtained by independent analysis for example, then the number of particles detected over a period of time can be related to the mass of dust that has passed through the measurement section during that time. From this, the concentration of the dust cloud in terms of $\mu$g per cubic metre can be determined.

Since the particles pass through the measurement section individually, the magnitude of the charge on each individual particle can be derived by individual on line integration of the current induced on the sensing electrode. The resulting output will therefore be related to the surface area of the particle which is related to the particle size. This is of particular importance in detecting small particles which constitute a health hazard. Since particle size can be sensed in this way, it is possible to derive an indication of the dust concentration, in terms of $\mu$g per cubic metre, without requiring information as to the particle size distribution in the dust being measured.

The invention as is defined above provides a technique whereby individual particles of a dust cloud can be passed through a measurement section containing sensing electrodes and be individually sensed and counted so as to provide (in conjunction with a particle size analysis of the target dust) an indication as to dust concentration in terms of $\mu$g per cubic metre. The invention also provides a technique of inducing (or placing) charges on individual dust particles proportional to their surface area so that they may be detected in cases where the magnitude of normally occurring charge on individual particles is too small to be detected. It allows the individual processing of the signal produced by each individual particle so as to obtain an indication of the individual particle sizes, and it provides a technique of deriving an indication of the dust concentration in terms of $\mu$g per cubic metre, from the measured individual particle sizes.

The organization and manner of the structure and operation of the invention, together with further objects and advantages thereof, may best be understood by reference to the following description, taken in connection with the accompanying drawings, wherein like reference numerals identity like elements in which.

Figure 6A:
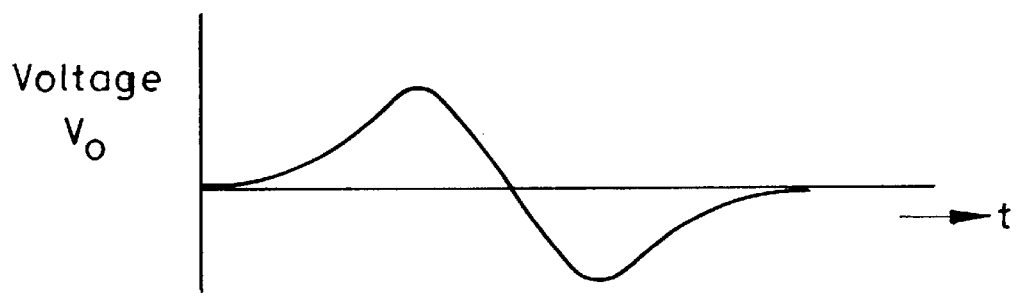
Figure 6B:
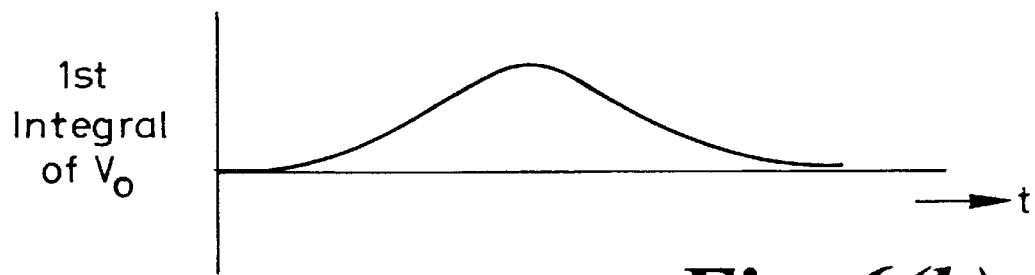
Figure 6C:
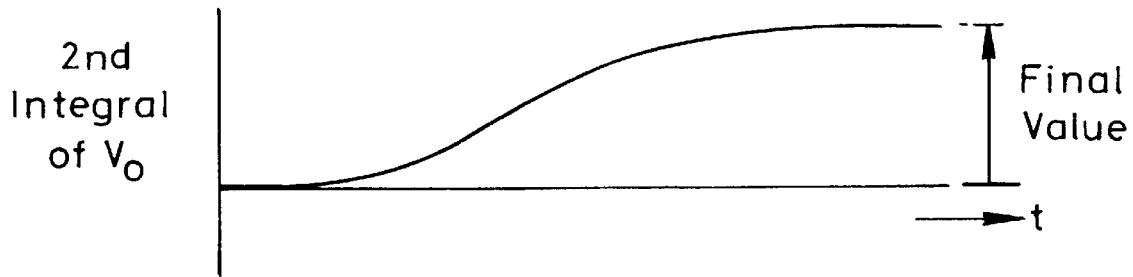

FIGS. 6(a) to 6(c) are illustrative of the signal processing requirement; and

Figure 7A:
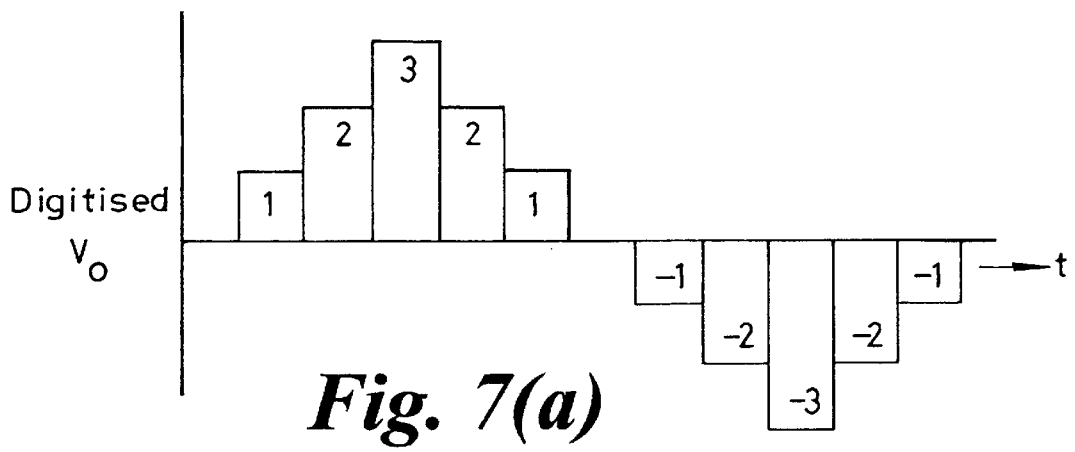
Figure 7B:
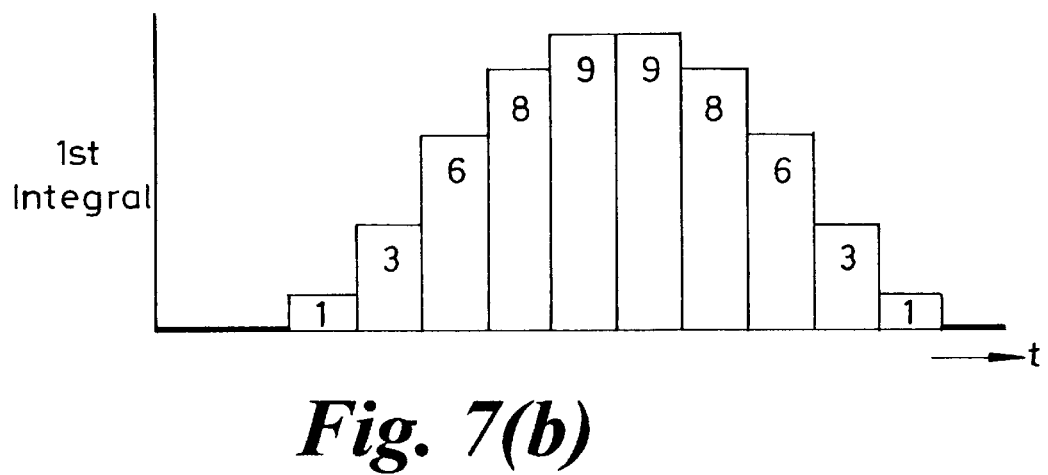
Figure 7C:
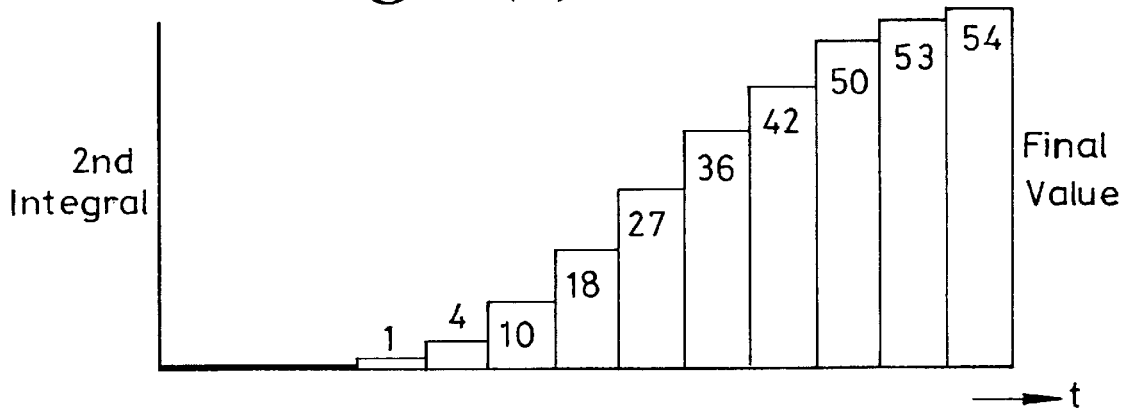

FIGS. 7(a) to 7(c) illustrate the sequence of values of digitised output voltage against time along with their first and second integrals.

DESCRIPTION

Figure 3A:
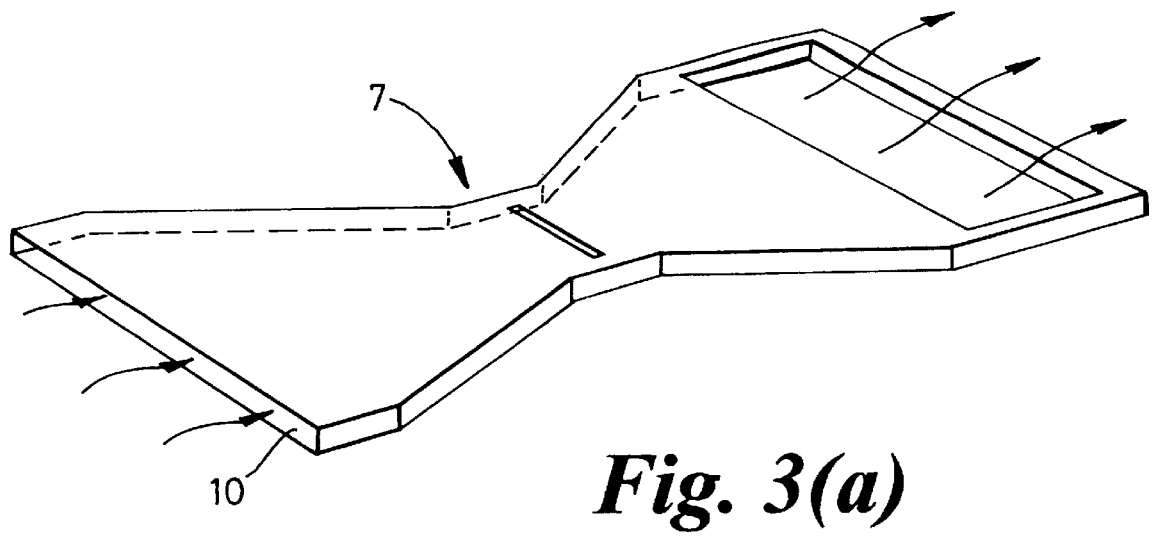
FIG. 3(a) is a schematic perspective view of ducting and associated measurement section.

In FIGS. 3(a) and (b) a sample of the air or gas in which the particles are suspended flows through a measurement section 7 comprising of a narrow duct 8 having electrodes attached to the outside of the insulating section 9 of the wall at the centre of the narrow section. The dimensions of the narrow section are arranged so that there is a high probability that at any particular time there is never more than one particle passing the sensing electrode, as described below. The individual signals produced by the separated particles may be counted over a period of time and the number of particles counted will therefore give an indication as to the number of particles present in the volume of air passed through the system in the particular period.

Figure 3B:
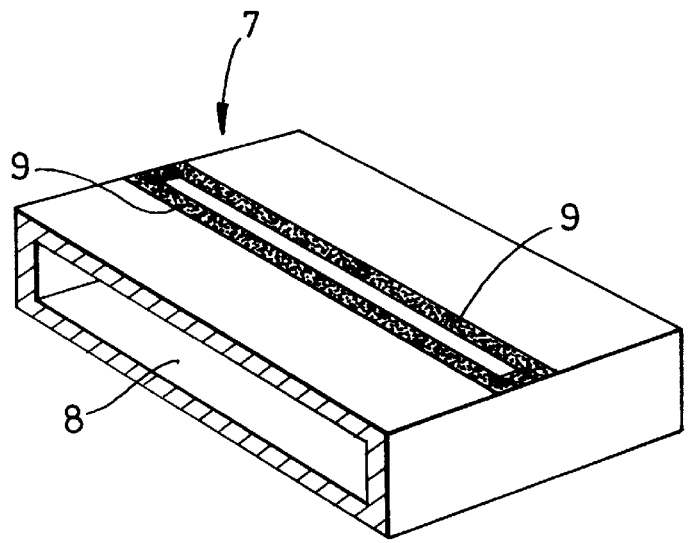
FIG. 3(b) is an enlarged sectional perspective view of the measurement section of FIG. 3(a)

In FIG. 3(a) a sample of the air containing the particulate material is drawn in through the inlet aperture 10, by the action of the extraction fan, which narrows down to a narrow channel that comprises the measurement section 7 where the sensing electrodes are mounted. A more detailed illustration of the measurement section is shown in FIG. 3(b).

In a particular application suppose that there was a concentration of 100 $\mu$g of particulate material per cubic meter of air. Suppose also that all of the particles were spherical in shape with a diameter of 5 $\mu$m and that the specific gravity was 2 (ie. the density of the material was 2 tonnes per cubic meter)

The total number $N_t$ of spherical particles of material in a 100 $\mu$g mass of material and therefore number of particles in a cubic meter will be:

$N_t = 7.64 \cdot 10^5$ particles per cubic meter

In FIG. 3 the cross section of the narrow channel in which the electrode is situated is 1 mm high and 10 mm wide. The effective length of the measurement volume is considered to be 6 mm in length, which is 3 mm upstream and 3 mm downstream of the sensing electrode namely a distance which is three times the width of the channel at the position of the electrode. Any charged particle outside of these limits has less than one tenth of the effect of a particle situated over the electrode, and can be considered not to be interfering with a signal produced by a particle in the measurement volume.

The volume V of air in the measurement volume is:

$V = 60 \cdot 10^{-9} \ m^{-3} (= 60 \ mm^3)$

The average number of particles $N_s$ in this space will be:

$N_s = N_t V$ which evaluates to:

$N_s = 0.046$

Since this figure is less than one there will, on average, never be more than one particle in the measurement volume at any one time so that the particles will be individually detectable.

The limiting condition for individual particle detection occurs when there is, on average, one particle in the measurement volume, ie one particle in each 60 mm$^3$ volume of air. This condition is reached for a concentration of 100 $\mu$g per cubic meter with a specific gravity of 2, when the particle size is 1.8 $\mu$m.

In practical dust clouds, particles are of varying size, therefore in order to calibrate the instrument in terms of $\mu$g of dust passing through it is necessary to know the particle size distribution of the dust and the specific gravity. These parameters may be found by independent analysis of a sample of the dust.

An alternative way of calibrating the instrument would be to run the instrument alongside a conventional dust pump for an extended period of time and relate the number of particles counted in the instrument with the mass of dust collected in the dust pump.

Figure 2A:
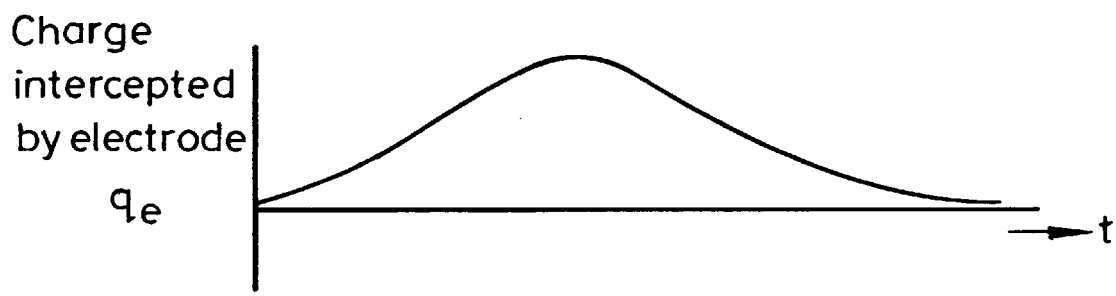
FIG. 2(a) is a graph of the charge intercepted by electrode $q_e$ plotted against time.
Figure 2B:
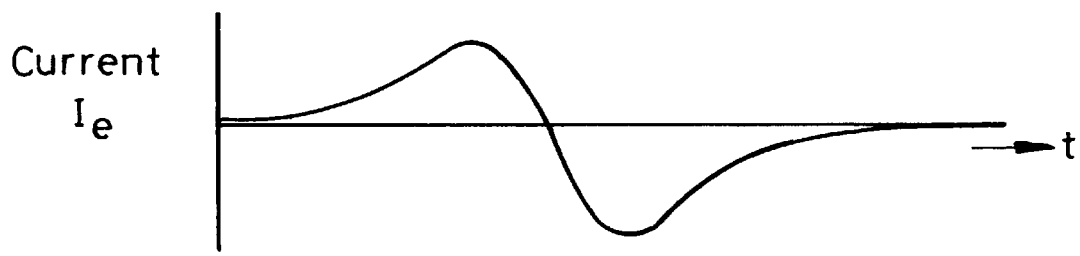
FIG. 2(b) is a graph of the current $I_e$ plotted against time.

The reduction of cross sectional area through the measurement section also has the advantage of increasing the velocity of the particles as they pass the electrode which has the effect of increasing the amplitude of the current and voltage waveforms I and Vo shown in FIGS. 2(a) and (b) due to the derivative action described in equation (1). This assists in the detection process.

Figure 4:
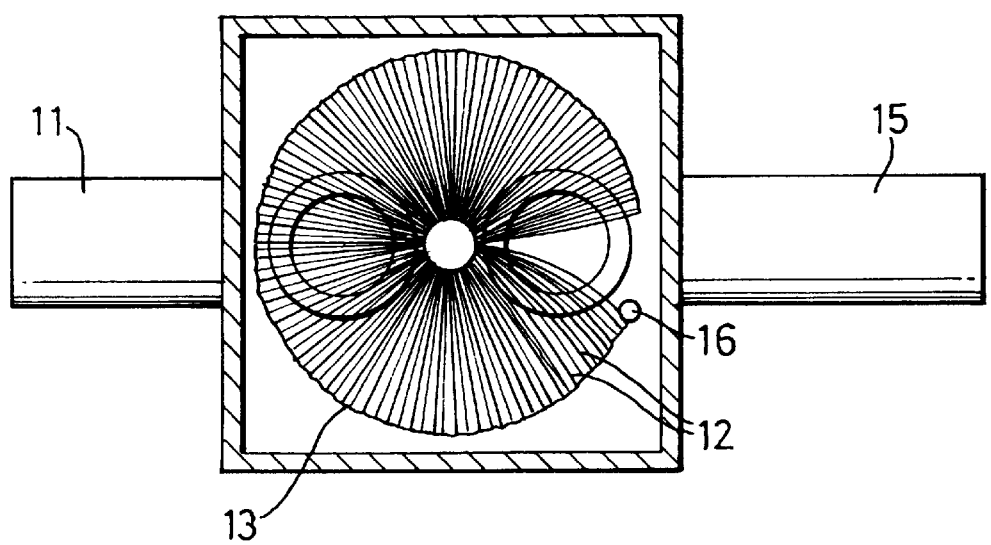
FIG. 4 is a schematic representation of charge induction means.
Figure 5:
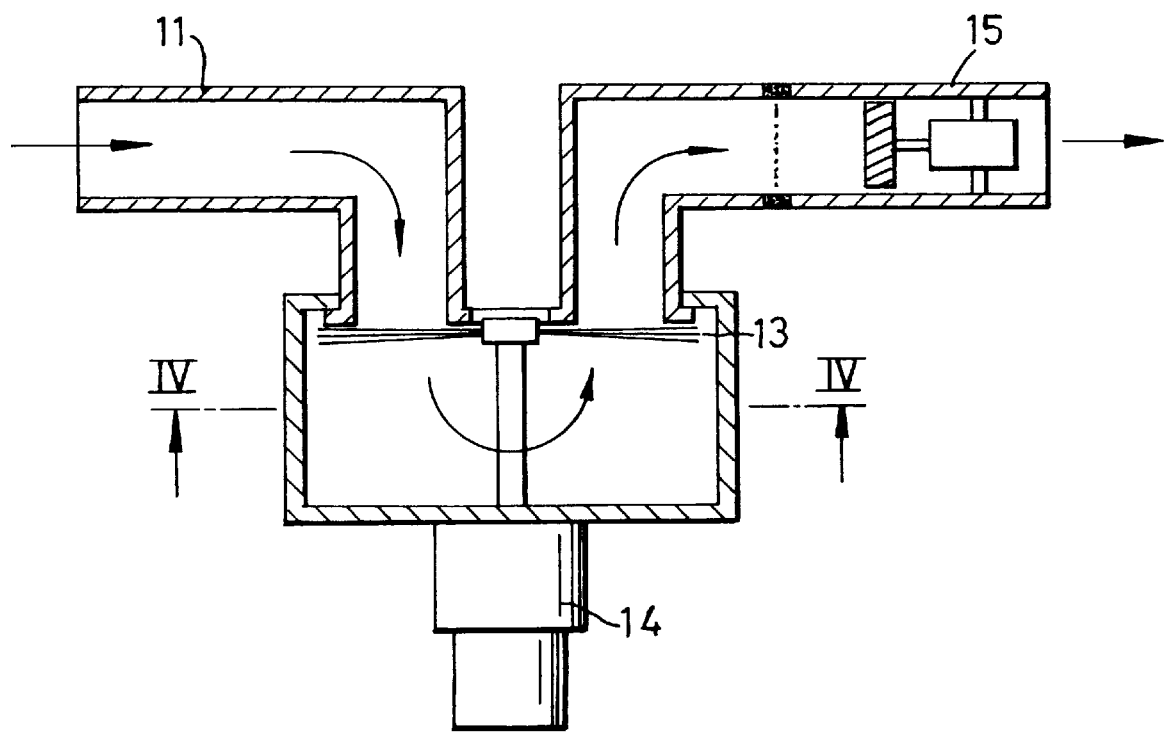
FIG. 5 is a section on the line IV—IV of FIG. 4.

As is illustrated in FIGS. 4 and 5, air containing the suspended particulate matter, the concentration of which is to be measured, is drawn in through the induction port 11 and the particles are trapped on the fibres 12 of a rotating filter 13 driven by a motor and gearbox 14. The cleaned air passes through the filter into the chamber and back through the rotating filter into an exit port 15.

As the filter rotates the tips of the fibres 12 are temporarily caught by a fixed peg 16 and as the filter continues to rotate, the individual fibres 12 are flicked over the exit port. This action releases the particles that were trapped on the filter to be re-entrained by the air passing from the chamber into the exit port.

The action of trapping the individual particles on the filter fibres and releasing them back into the air stream, will impart charges on the particles due to the action of friction between the fibres and the fixed peg and between the fibres and the particles lodged on them. In general terms, the charge induced on particles by friction is a function of the surface area of the particle.

The effect may be enhanced by arranging that the peg is maintained at a high voltage with respect to earth.

The output from the charge induction mechanism is then fed to the charge sensing mechanism as described in the first embodiment.

In order to measure the value of charge on each individual particle it is necessary to double integrate the signal produced from the electrode as each charged particle passes.

Figure 1:
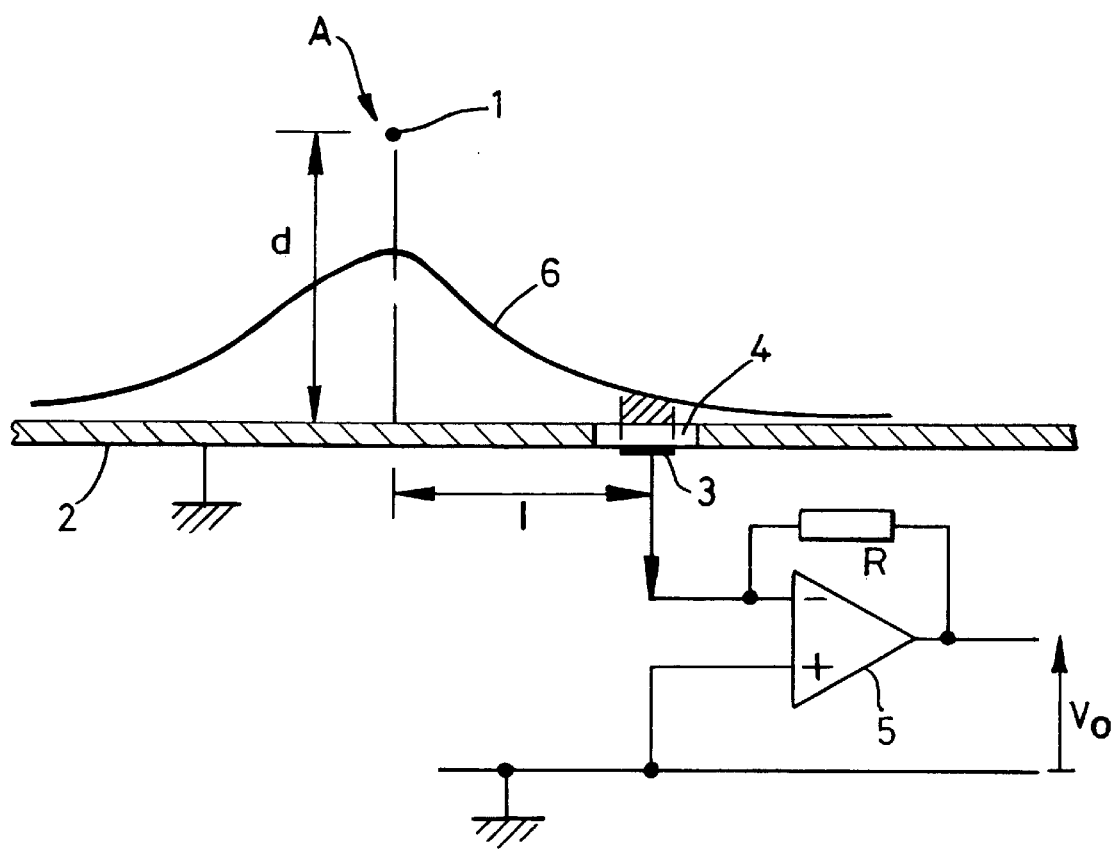
FIG. 1 is a schematic sectional elevation of the volume below a charge distribution curve.
Figure 2C:
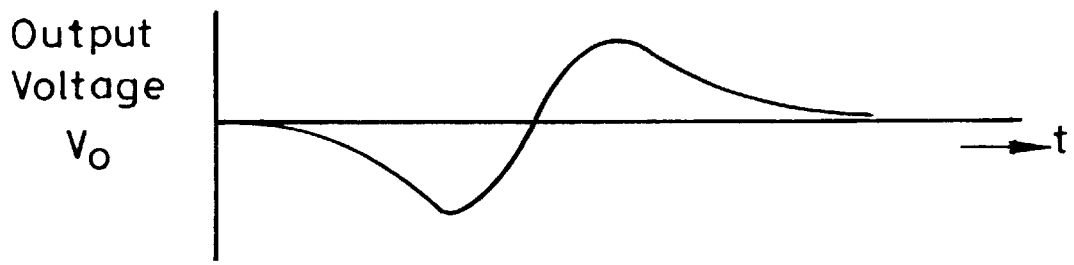
FIG. 2(c) is a graph of the output voltage $V_o$ plotted against time.

The operational amplifier circuit arrangement shown in FIG. 1 is used to produce a voltage waveform Vo at it's output of the form shown in FIG. 2(c) which is proportional to the time derivative of the charge induced on the electrode as the charged particle moves past at constant velocity.

The output voltage from the amplifier is then sampled at high speed with an analogue to digital converter and the resulting digitised version of the analogue signal $V_o$ are stored sequentially in a section of memory. As an example suppose samples were taken every 20 μs and stored in 250 sequential locations of memory, the memory being over-written again when full. This would mean that at any given time a record would always exist of the last 250 samples which represents the last 5 ms of output voltage.

The diagrams of FIG. 6 illustrates the signal processing required. FIG. 6(a) shows the voltage waveform at the output of the operational amplifier and is similar to the waveform shown in FIG. 2(c) but is shown without inversion for the sake of clarity.

FIG. 6(b) shows the effect of integrating the voltage waveform of FIG. 6(a) with respect to time and which is proportional to induce charge on the electrode with respect to time. The area under this waveform is proportional to the charge on the particle and to derive this value the waveform of FIG. 6(b) is integrated with respect to time. This waveform (as a function of time) is shown in FIG. 6(c) and the final value of this waveform is proportional to the area under the waveform of FIG. 6(b) and therefore the charge on the particle.

In practice the integration processes described above are most easily achieved by digital signal processing on the numerical values stored sequentially in memory as described above. To illustrate the mechanism further (using a simple example), suppose the sequential digitised values of the amplifier output voltage $V_O$ caused by the passage of a charged particle past the electrode system are as given in the first row of Table 1 below.

This sequence of values is plotted as a time sequence in the diagram of FIG. 7(a).

The numerical integration of this sequence of values, as derived by the cumulative addition of the values given in row 1 of the Table 1, are given in the second row of Table 1, and are plotted in FIG. 7(b).

The second integration of these values, as derived by the cumulative addition of the values in row tow of Table 1, are given in row 3 of Table 1 and are plotted in FIG. 7(c).

TABLE 1

| Signal | 0 | 1 | 2 | 3 | 2 | 1 | 0 | −1 | −2 | −3 | −2 | −1 | 0 |
|---|---|---|---|---|---|---|---|---|---|---|---|---|---|
| 1st Int | 0 | 0 | 1 | 3 | 6 | 8 | 9 | 9 | 8 | 6 | 3 | 1 | 0 |
| 2nd Int | 0 | 0 | 0 | 1 | 4 | 10 | 18 | 27 | 36 | 42 | 50 | 53 | 54 |

The final value of this process is the numerical value 54 which represents the value of the charge on the particle.

It is important that both the integration processes start before the pulse arrives at the output of the operational amplifier and this will be possible because there is always a historical record of the last 5 ms of signal available in the sequential memory.

The process will involve detecting when the output voltage signal from the amplifier has risen above a pre-arranged threshold indicating that a charge particle is approaching the sensing electrodes, and then beginning the two integration processes outlined above from an appropriate historical point in the memory, so as to take account of the beginning of the pulse, and continuing until the pulse has passed. The final double integrated value may then be further processed as described below.

It should be noted that the process of obtaining a value proportional to the charge on the particle is independent of the position of the particle from the electrodes. Although the shape of the induced charge on the earthed plane varies according to the distance from the plane as is indicated in FIG. 1 (and therefore so does the shape of the induced charge vary with respect to time) the area under these curves (ie. the integral of the waveform with respect to time) will be the same and proportional to the magnitude of the charge on the particle.

The charge on each particle is likely to be proportional to the surface area of the particle particularly if the charge inducing or placing mechanism is used prior to the sensing mechanism. Therefore the measured value of the charges may be classified into bands which will allow the number of particles in each size band to be derived over a long measurement period.

Assuming that the particles are spherical in shape, the mass of a particle will be proportional to the cube of the diameter, whereas the surface area is proportional to the diameter squared. Since the charge detected on each particle is likely to be proportional to the surface area the relative masses of the individual particles may be found by raising the measured charge values to the power of 3/2.

What is claimed is:

1. A method of monitoring dust or particulate material concentrations in air, characterised by drawing air through a monitor at a predetermined rate to enable particles to pass through a measurement section one at a time, whereby they may be individually detected and counted, there being an electrode located in the measurement section on which an individual particle induces a pulse of charge, and there being a means of counting the number of pulses of charge induced on the electrode in unit time, from which the concentration of dust particles in the air in the vicinity of the monitor can readily be derived.

2. A method of monitoring dust/particulate material concentrations in air as in claim 1, characterised in that there is provided a means of inducing a charge on the particles as they pass through it.

3. A method of monitoring dust/particulate material concentrations in air as in claim 2, characterised in that a rotating filter is provided in the flow path from an inlet to the measurement section, whereby particles are first caught and then thrown from the filter, to induce a charge on an uncharged particle or increase the charge on a charged particle by the tribo-electric effect, the degree of induced charge being proportional to their surface area, whereby to enable a pulse of charge to be induced on the electrode.

4. A method of monitoring dust/particulate material concentrations in air as in claim 1, characterised in that a fan is employed to draw air through the monitor in required volumes.

5. A method of monitoring dust/particulate material concentrations in air as in claim 1, characterised in that a digital recording means for storing the shape and count of pulses for subsequent analysis is provided.

6. A method of monitoring dust/particulate material concentrations in air as in claim 1, characterised in that a visual or audible signal means to warn an operative that a predetermined level of dust concentration in the air has been reached.

* * * * *